United States Patent
Vasin

(10) Patent No.: US 9,033,712 B2
(45) Date of Patent: May 19, 2015

(54) TRAINING METHOD AND A DEVICE FOR CARRYING OUT SAID METHOD

(76) Inventor: Maxim Alexeevich Vasin, Moscow (RU)

(*) Notice: Subject to any disclaimer, the term of this patent is extended or adjusted under 35 U.S.C. 154(b) by 1110 days.

(21) Appl. No.: 12/664,213

(22) PCT Filed: Jun. 5, 2008

(86) PCT No.: PCT/RU2008/000347
§ 371 (c)(1),
(2), (4) Date: Dec. 11, 2009

(87) PCT Pub. No.: WO2009/002218
PCT Pub. Date: Dec. 31, 2008

(65) Prior Publication Data
US 2010/0173276 A1    Jul. 8, 2010

(30) Foreign Application Priority Data

Jun. 18, 2007   (RU) ................................ 2007122577

(51) Int. Cl.
*G09B 19/00*       (2006.01)
*A63B 24/00*       (2006.01)
(Continued)

(52) U.S. Cl.
CPC ............ *A63B 24/0006* (2013.01); *G09B 19/00* (2013.01); *A61N 1/00* (2013.01);
(Continued)

(58) Field of Classification Search
CPC ............ G09B 5/00; G09B 7/00; G09B 19/00
USPC ........................................................ 434/258
See application file for complete search history.

(56) References Cited

U.S. PATENT DOCUMENTS

| 3,644,919 A | 2/1972 | Mathauser |
| 4,337,049 A | 6/1982 | Connelly |

(Continued)

FOREIGN PATENT DOCUMENTS

| RU | 2107328 CI | 3/1998 |
| RU | 2266144 C2 | 12/2005 |

(Continued)

OTHER PUBLICATIONS

Partial English translation of SU 1491444 A1.
(Continued)

*Primary Examiner* — Xuan Thai
*Assistant Examiner* — Michael Grant
(74) *Attorney, Agent, or Firm* — Ladas & Parry LLP

(57) ABSTRACT

The invention relates to training and can be used for learning and/or developing movement skills, fixing dynamic stereotypes and for training movement coordination. The aim of the invention is to provide a trainee with on-line correcting tactile feedback during training and to improve techniques and rate of a movement by bringing it as close as possible to a reference movement. The inventive training method consists, when learning a movement, in digitizing said movement, in comparing it with the digitized pattern of a reference movement and, if the trainee deviates from the reference movement, in receiving by said trainee a tactile feedback (tactile action) for on-line correcting said movement. The inventive device comprises sensors for on-line movement digitizing, a computer for comparing the thus obtained digitized movement with the reference movement (specified by an expert or simulated on the computer) for controlling the tactile feedback elements and said tactile feedback elements for performing the correction action.

55 Claims, 4 Drawing Sheets

A-A
Variant 1

A-A
Variant 2

(51) Int. Cl.
*A63B 69/00* (2006.01)
*A61N 1/00* (2006.01)
*G09B 5/00* (2006.01)
*G08B 23/00* (2006.01)
*G09B 7/00* (2006.01)
*A63B 71/06* (2006.01)

(52) U.S. Cl.
CPC ............... *G09B 5/00* (2013.01); *G08B 23/00* (2013.01); *G09B 7/00* (2013.01); *A63B 69/004* (2013.01); *A63B 71/0686* (2013.01); *A63B 2024/0012* (2013.01); *A63B 2024/0015* (2013.01); *A63B 2071/0655* (2013.01); *A63B 2220/51* (2013.01); *A63B 2220/803* (2013.01); *A63B 2220/805* (2013.01); *A63B 2220/836* (2013.01); *A63B 2244/22* (2013.01)

(56) References Cited

U.S. PATENT DOCUMENTS

| | | | |
|---|---|---|---|
| 5,372,365 A | | 12/1994 | McTeigue et al. |
| 5,679,004 A | * | 10/1997 | McGowan et al. ........... 434/247 |
| 5,826,578 A | * | 10/1998 | Curchod ....................... 600/595 |
| 5,941,779 A | | 8/1999 | Zeiner-Gundersen |
| 2002/0077189 A1 | | 6/2002 | Tuer et al. |
| 2003/0125781 A1 | * | 7/2003 | Dohno et al. .................. 607/75 |
| 2004/0077975 A1 | * | 4/2004 | Zimmerman ................. 600/595 |
| 2004/0212673 A1 | | 10/2004 | Sudo |
| 2005/0181347 A1 | * | 8/2005 | Barnes et al. ................. 434/350 |
| 2006/0022833 A1 | | 2/2006 | Ferguson et al. |
| 2006/0024647 A1 | * | 2/2006 | Chesnais et al. .............. 434/114 |
| 2009/0023122 A1 | * | 1/2009 | Lieberman et al. ........... 434/258 |

FOREIGN PATENT DOCUMENTS

| | | |
|---|---|---|
| SU | 797708 A | 1/1981 |
| SU | 1491444 A1 | 7/1989 |
| SU | 1798809 A2 | 2/1993 |

OTHER PUBLICATIONS

Partial English translation of U 797708A.
Partial English translation of RU 2107328 C1.
Partial English translation of SU 1798809 A2.
Partial English translation of RU 2266144 C2.
Acrosport.ru publication "siliconCoach", unknown author, 2008, 2 pages, http://www.aerosport.ru/items/zifrovie-tehnologii/video.htm.

* cited by examiner

A-A
Variant 1

A-A
Variant 2

TRAINING METHOD AND A DEVICE FOR CARRYING OUT SAID METHOD

TECHNICAL FIELD

The invention relates to training and can be used for learning and/or developing movement skills, fixing dynamic stereotypes and for training movement coordination.

The invention can be applicable for practicing movements in different sports, combat sports, dancing, for training theater actors, ballet dancers, circus performers, in games, and the likes.

BACKGROUND OF THE ART

There are a lot of activities requiring possessing specific movement skills in a varying degree. These activities may cover dancing, sports, martial arts, theater, dumb show, dramatic activity and some others. The physiological bases for learning movement skills consist in forming unstable temporary links between nerve centers regulating the activity of different muscles and organs at the starting stage of training movements in CNS. At a later stage these links are differentiated and consolidated.

Developing a movement skill it is conventional to divide into three stages.

The first stage is characterized in that, when learning a new movement, the physical movements are poorly coordinated and are technically inefficient.

The concentration of excitement in certain centers of the nervous system is the basis for the second stage of developing said skill.

The third stage of developing said movement skill is the freedom of movements, high degree of coordination and stabilization thereof.

The multiple performing of exercises in strictly-defined order generates a dynamic stereotype. Generating a dynamic stereotype requires long laborious training The stability of performing movement skills is very closely associated with the degree of mastering thereof. As other conditioned reflexes, the movement skills are insufficiently stable at the beginning, but in future become increasingly stable. The simpler skills in their structure are, the faster they learn. The main problem of a trainee at the starting stage of learning complex-structured movements is the coordination of all the parts of bodies in the process of practicing movements to generate a true dynamic stereotype.

The common practice in the process of learning one or other movement action is a multiple repetition thereof under leadership of a trainer who corrects movement trajectories of different parts of body to gain technically perfect performance. After the movement stereotype is fixed, the rate and freedom in executing an action is instilled. It is obvious that achieving a success with this approach primarily depends on the trainer's competence and mastery. Moreover, this approach is effective for a limited number of trainees with one trainer, as the number of trainees in the group increases, the training efficiency with a trainer falls.

From the art known are video analysis systems for learning sport movements and improving techniques of movement actions (for example, the SiliconCoach Company's project. The video analysis systems use an athlete's video record to analyze different phases of his movement (trajectories, angles and rates see http://www.acrosport.ru/items/zifrovie-tehnologii/video.htm), as well as to compare the trainee's movement with the movements of professional athletes in order to correct them.

The main disadvantage of such systems is the absence of feedback directly in the process of performing a movement (the trainee does not feel a right trajectory in the process of training) declining thereby the efficiency of training. Another disadvantage declining the training efficiency is that the feedback is provided via a visual channel (on a monitor screen). In the process of transferring a video sequence and pictures to own movements, a trainee may get considerable distortions. Moreover, the trainee's movement information requires previous manual processing.

DISCLOSURE OF THE INVENTION

The aim of the invention is to provide a trainee with on-line correcting tactile feedback during training and to improve techniques and rate of a movement by bringing it as close as possible to a reference movement. The inventive training method consists, when learning a movement, in digitizing said movement, in comparing it with a digitized pattern of a reference movement and, if the trainee deviates from the reference movement, in receiving by said trainee a tactile feedback (tactile action) for on-line correcting said movement.

According to another embodiment of the invention, the inventive device for implementing said training method comprises sensors for movement digitizing, a computer for comparing the thus obtained digitized movement with the reference movement and the tactile feedback elements for on-line correcting a trainee's movement.

Reference movement patterns can be specified either by an expert skilled in this art (for example, an athlete) using some recording equipment, or simulated by the computer.

If, when learning a movement, one or another part of body of a trainee goes beyond the admissible deviation corridor from the specified trajectory (See FIG. 2(1)), the trainee receives a signal about it by switching on a tactile feedback element in the zone where a critical deviation occurred (See FIG. 2). The signal can be thereby fed from the side toward which said deviation occurred (as if "pushing" a part of body out of the forbidden zone (FIG. 2(2)), or from the side where said part of body should return (as if "pulling" it in). This allows actually immediately to correct the whole set of trainee's movements with minimum engaging or with no engaging at all an expert (a trainer) in the process of training. The intensity of the tactile action depends on the deviation rate growing as the deviation increases.

BRIEF DESCRIPTION OF THE DRAWINGS

The invention as set forth is illustrated by graphic presentations which show.

DETAILED DESCRIPTION OF THE INVENTION

The training method can be illustrated by the following example.

Figure 1:
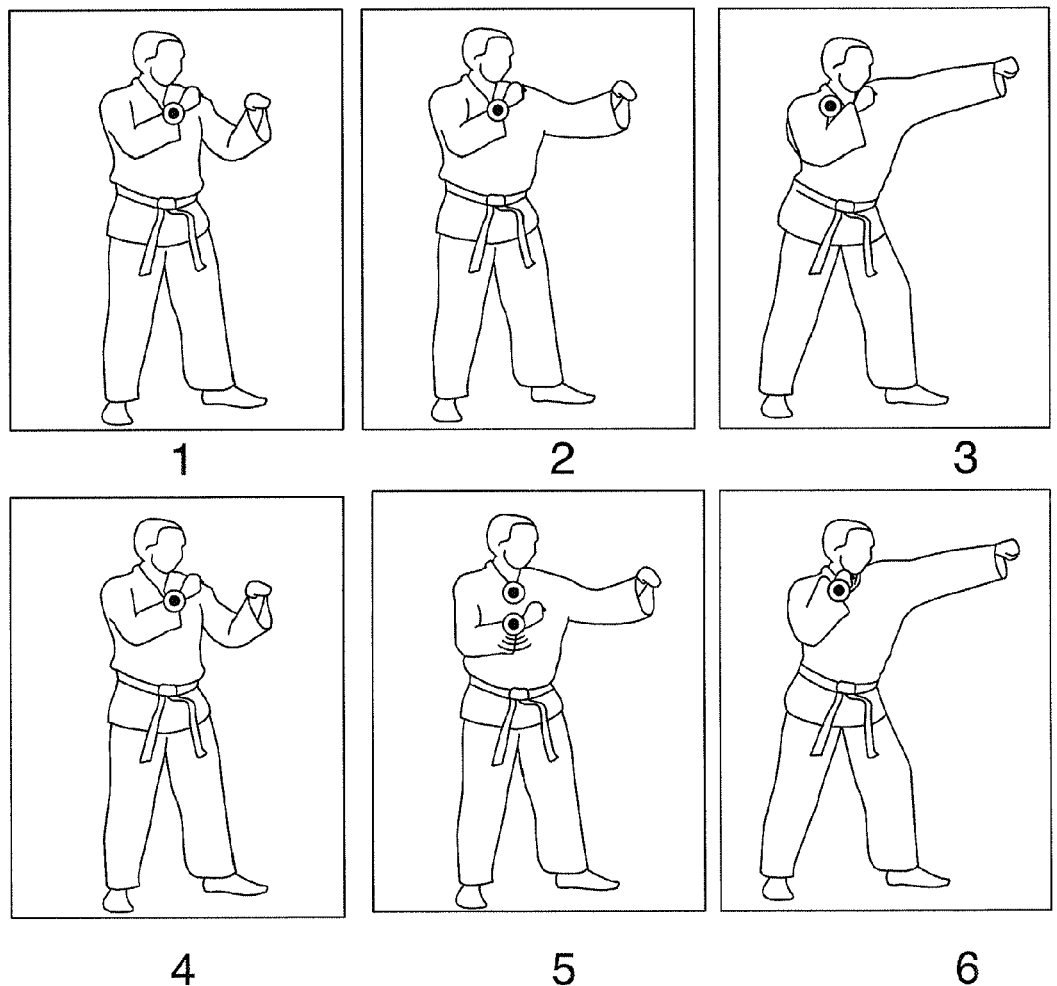
FIG. 1 is a tactile correction action in the process of learning a movement.

When learning martial arts, one of the most common errors of beginners is when practicing a blow with one arm they forget that the other arm should provide the face protection. The right position of the other arm during practicing a blow is shown in FIG. 1(1-3). When practicing a blow, a novice athlete often lets down the other arm (FIG. 1(5)). In this case, as soon as the arm providing protection lets down below the critical point, the tactile signal of the feedback element actuates from the downside of the hand making the arm return to the right position (FIG. 1(5-6)).

The coordinated work of all the parts of body can be attained by transferring a tactile deviation signal of one or another part of body from the specified trajectory. A trainee concentrated on a leg's movement will not forget any more about position of arms, as the tactile signal will remind him of a deviation right there.

The movement pace is set by a sound, visual or tactile signal (background music, a single sound signal repeated at a certain pace, video sequence, light indicator blinking, periodic oscillations, etc.).

Variants of carrying out training:

1. In combination with a video course—movements to be repeated are specified by a video sequence, the digitized pattern of a reference movement is previously created and enclosed to the video course;

2. In combination with personal computer (PC) software. This variant will allow to synchronize the video sequence (on a PC monitor) setting movements and the digitized pattern of a reference movement, to keep statistics and perform an analysis of movements on a PC screen;

3. Autonomously, when as a reference movement a trainee sets the movement which he performs by himself.

4. In groups when a movement on-line specified by one person (for example, a trainer) becomes reference for another/other persons. Thus, joint training of people being in one room or being far apart can be organized (through telecommunication technologies). It is sufficient for the trainer to do right movements—all of the errors in trainees' movements will be immediately corrected via tactile feelings.

5. In combination with virtual reality complexes to bring some diversity into training and to immerse a trainee more deeply into the training process.

To achieve said technical result, the inventive device (further referred to as "TRAINING SIMULATOR") comprises sensors for on-line movement digitizing, a computer for comparing the thus obtained digitized movement with the reference movement (specified by an expert or simulated on the computer) for controlling the tactile feedback elements and said tactile feedback elements for performing the correcting action.

The TRAINING SIMULATOR can comprise the following main elements:

spatial motion sensors of a trainee's body parts for movement digitizing which can be, for example, visual, magnetic, mechanical sensors, micromechanical accelerometers, gyroscopes, other types of sensors determining the spatial position of body parts, or combinations thereof. Certain attaching points of sensors, their numbers and constitution depend on the specifics of the movements studied;

tactile feedback elements in capacity of which, for example, vibro, thermal elements, current discharges, other elements providing the tactile action can be used. Certain points of action of the feedback elements, their number and constitution depend on the specifics of the movements performed;

a computer (a computing unit) implemented, for example, on the basis of a pocket PC, nonremovable PC or implemented as a specialized device is required to process signals from the motion sensors, to convert the sensor signals to a digitized movement pattern, to compare the reference movement with a user's movement, to control the feedback elements, etc.

a memory unit storing information about the reference pattern of the movement being leant can be used in order to store a trainee's movement for further use (as a reference movement pattern, for analyzing with the aid of computing facilities, etc.), it is optional if the training is carried out in a condition when a trainer performs a movement, and a trainee repeats it—in this case the trainer's digitized movement passes to the trainee's training simulator as a reference movement pattern immediately and without storing;

a data bus line for transferring information between the TRAINING SIMULATOR elements, several TRAINING SIMULATORs and between the TRAINING SIMULATOR and external devices (wired or wireless, for example, by the Bluetooth technology or using Microchip rfPIC™ chips);

a power supply source for the TRAINING SIMULATOR (for example, accumulator cells) can be both single for all the TRAINING SIMULATOR elements, and individual for each element/group of elements.

The list of the TRAINING SIMULATOR components given above is approximate, as there can be a plurality of the TRAINING SIMULATOR integration variants and it depends on the specifics of the movements to be learnt and mechanisms of providing training material. So, the TRAINING SIMULATOR can be comprised of sensors of pressure on a foot and elements signaling the surplus and the lack thereof, mechanisms synchronizing the TRAINING SIMULATOR with the personal computer which can serve as a screen for the training video sequence and other components providing expanding its service functions and more comfortable work with the TRAINING SIMULATOR.

Operation algorithm with the TRAINING SIMULATOR is following:

1. The reference pattern of a movement skill is created with the aid of specialized software or taken from the expert's body (directly by using the TRAINING SIMULATOR or a simplified variant thereof in which the feedback elements are absent; using other available means and methods).

2. The motion pattern made up at the first stage by some means or other is transferred to the memory unit which the computer unit of the trainee's TRAINING SIMULATOR is coupled to.

3. The trainee repeats the movements being learnt specified, for example, by the video sequence or shown by the teacher or presented in any other available way.

4. The TRAINING SIMULATOR traces the trainee's movements via the motion sensors and compares them with the reference movement obtained at stage 1. The most convenient zones for sensors and feedback elements to be placed are joint regions but other variants of placing are also possible.

Figure 2:
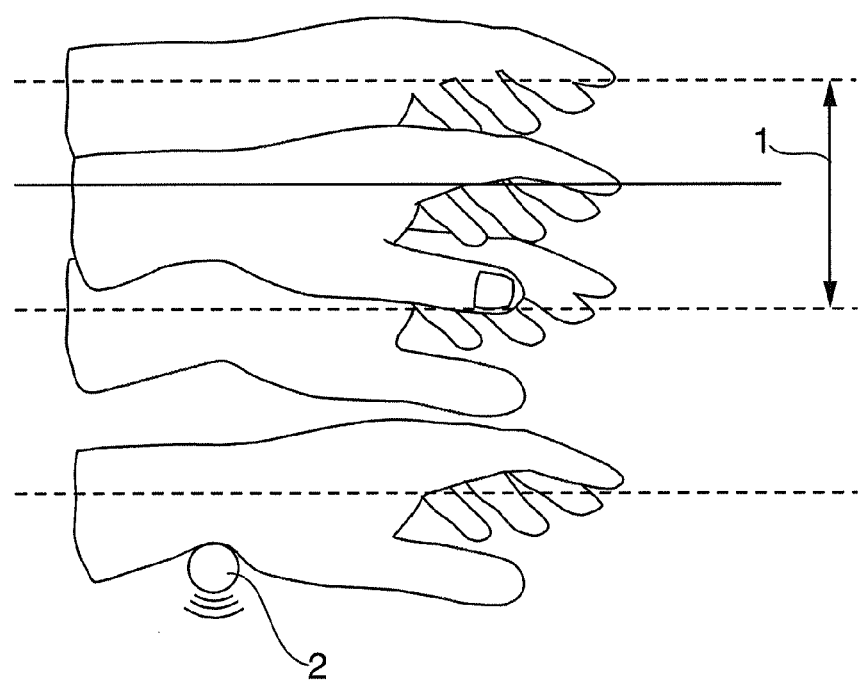
FIG. 2 is an illustration of the TRAINING SIMULATOR operation, when going a limb beyond the admissible deviation corridor.

5. With regard to the level of mastering the movement a so called "free zone" (or "a deviation corridor" FIG. 2(1)) can be specified—a zone within which the TRAINING SIMULATOR will not response to the difference between the reference movement and the trainee's movement.

6. When the trajectory of the movement of one or other sensor deviates from the reference movement to an inadmissible extent, the TRAINING SIMULATOR signalizes about it with the aid of a feedback element defining the zone within which said deviation took place and making the trainee to correct the movement in the process of performing it.

7. At the starting stage of learning the movement the TRAINING SIMULATOR may not response to a deviation within sufficiently great limits, but as the movement is mastered the free zone can diminish and as result, the TRAINING SIMULATOR corrects progressively smaller deviations from the reference movement.

8. In the process of training recording a three-dimensional pattern of trainee's movement is possible for further analyzing and comparing it with the reference movement on a PC monitor.

9. The implementation of the TRAINING SIMULATOR can provide for an opportunity of storing the movement pattern by recording a movement on one TRAINING SIMULATOR and transferring it to another TRAINING SIMULATOR as a reference movement in the process of training.

10. In case of the TRAINING SIMULATOR comprises a "Movement recording" condition, the user can use the TRAINING SIMULATOR in search of the most suitable movement for the activity chosen (dancing, dumb show, martial arts, etc.) switching it on for recording movements. Further the performed movement can be recovered by placing the TRAINING SIMULATOR in the training condition.

11. To analyze the accuracy of performing one or other high pace movement (when it is physically impossible in good time to response to the TRAINING SIMULATOR signals), to record a fast movement for further analysis is possible.

According to the requirements, the detailed embodiment of the present invention is stated herein; however, it should be clear the stated embodiment is just a possible embodiment of the invention which can be differently implemented. Therefore, the concrete structural and functional details stated herein should not be interpreted as confining but just as a basis for claims.

Additionally, the terms and phrases used herein are rather not intended to confine but to provide the understandable description of the invention.

For the persons skilled in this art it is obvious that the parts of the invention can be realized in hardware or in software or in combination thereof. The invention implementing programs or parts thereof can be stored on various kinds of computer-readable information media including optical disks, hard disk drives, tapes, programmable read-only memory microchips and some others. Network circuits also can temporarily serve as a computer-readable information medium from which programs meeting the principles of the present invention are read.

Figure 3:
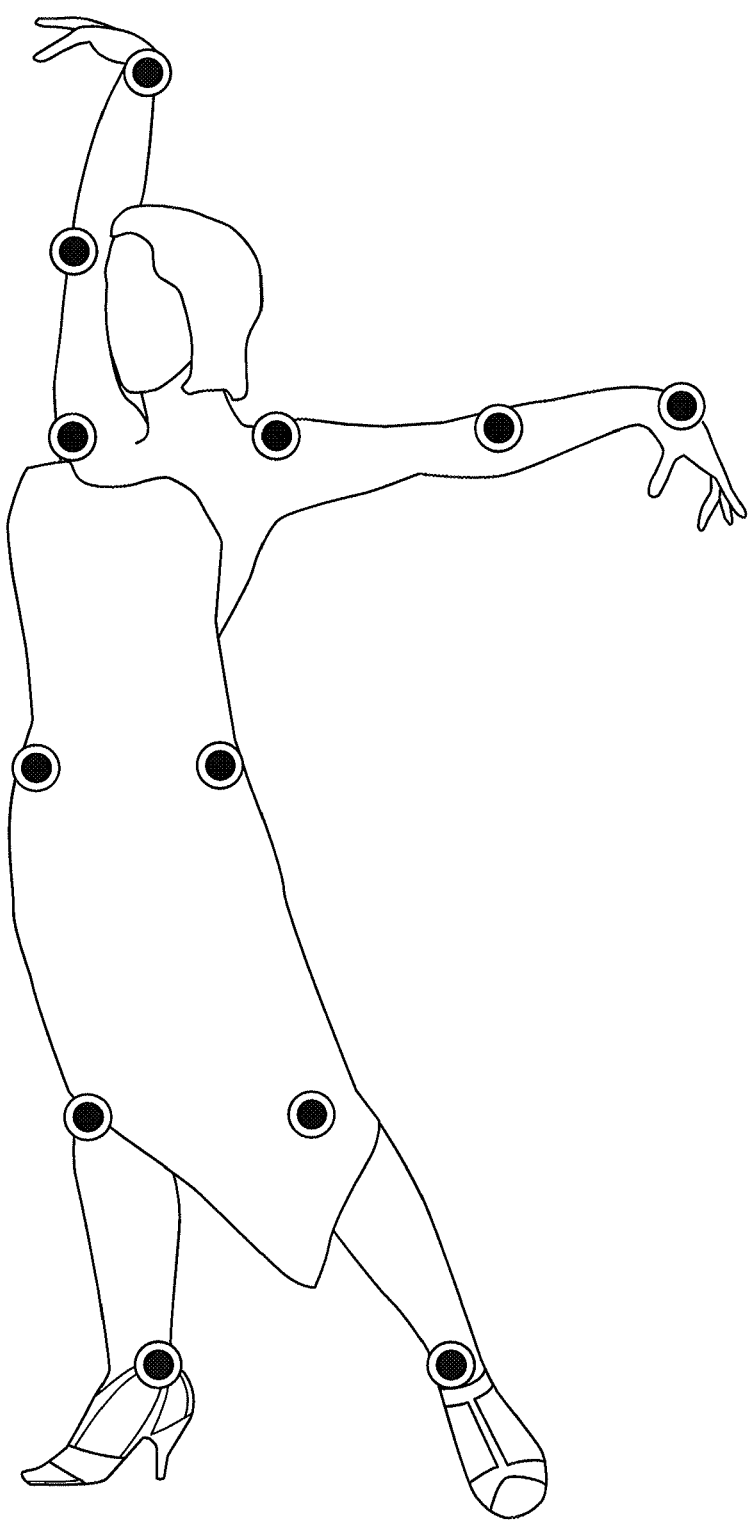
FIG. 3 is possible sites of motion sensors and feedback elements on a trainee's body.
Figure 4:
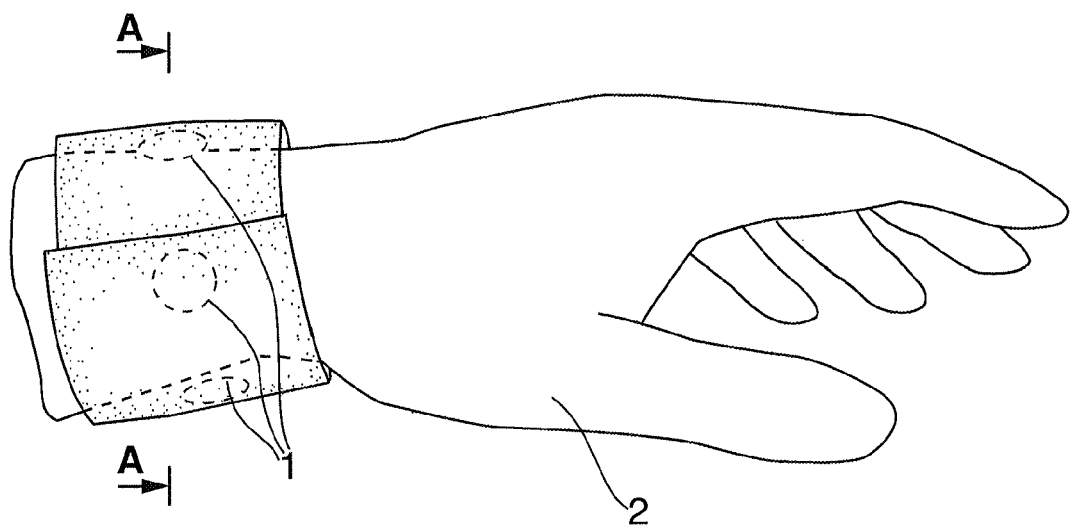
FIG. 4 is a possible site of a vibro-variant of the feedback elements on a limb.
Figure 4:
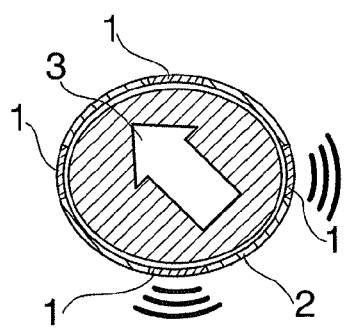
Figure 4:
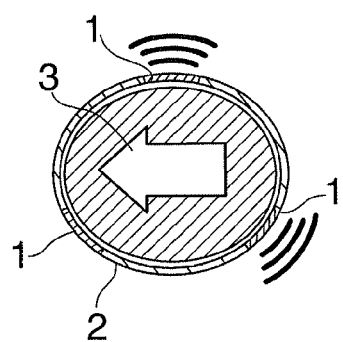

In the preferred embodiment, the TRAINING SIMULATOR corresponding to the present invention comprises the following basic elements:

Spatial motion sensors of trainee's body parts made on the basis of micromechanical accelerometers. The accelerometers are arranged in the region of main limb joints (FIG. 3) in groups, 3 pieces orthogonally and serve to set coordinates of each limb joint. Processing the accelerometer data is carried out with hardware-based means arranged within the motion sensor housing. The processing results are sensor coordinates (and a limb, respectively) which pass to the computing unit of the TRAINING SIMULATOR for further processing;

Tactile feedback elements which are individual or banked in groups of 2, 3 or more electromotors, on the shaft of each of them an eccentric is attached and a driving signal processing unit. The electromotors (FIG. 4(1)) are arranged evenly around a limb FIG. 4(2)) in the joint region. The combination of vibration elements switched on with different force specifies the direction (FIG. 4(3)) in which the limb should be motioned to return it to the right trajectory. The vibration elements are arranged in the region of the basic limb joints (FIG. 3).

The driving signal indicating which motor and at which rate should revolve (to produce a necessary tactile action) is received from the computing unit and processed by hardware tactile feedback means;

A motion sensor and feedback element unit attached on left wrist comprises a TRAINING SIMULATOR control panel.

A computing unit comprising a memory unit attached on a trainee's body;

A data bus line to transmit information between the TRAINING SIMULATOR elements implemented according to the Bluetooth technology;

The motion sensors and tactile feedback elements to trace one part of body in the preferred embodiment are designed within one body and have the common power supply source and a data bus interface forming a recording and feedback unit which can be attached on a body with the aid of "bur"-type fasteners.

The computing unit, memory unit, data bus interface and power supply source for them in the preferred embodiment are designed within one housing and form an evaluator which is attached in the trainee's belt.

In the preferred embodiment the TRAINING SIMULATOR operates as follows:

Via the data bus line the reference pattern of the movement to be leant is loaded in the TRAINING SIMULATOR. The TRAINING SIMULATOR is attached on a trainee's body. The trainee strikes a certain initialization pose (for example, standing upright, feet together, the left arm is put down along the body, the fingers of the right hand are in the wrist of the left hand) and performs the initialization of the TRAINING SIMULATOR by pressing the corresponding control panel key. After the initialization the trainee takes the starting position for the movement being learnt and starts performing it. The starting rate of movement performing is set on the TRAINING SIMULATOR control panel. The trainee's movements are traced by the TRAINING SIMULATOR sensors and compared with the reference movement pattern. If the trainee's movements do not correspond to the reference pattern, the TRAINING SIMULATOR corrects them feeding a tactile feedback signal to the relevant feedback units. If the movements are right performed, the TRAINING SIMULATOR, if required, increases the rate of performing the movement signalizing about each increase of the rate with a progressively increasing sound signal. If the movements at the required rate are right performed, the TRAINING SIMULATOR signalizes about it with a certain sound signal. The movement is considered to be learnt, one can proceed to learning the next movement or a set of movements.

It should be mentioned that tracing information of body part motions does not involve a fundamental difficulty, as the similar devices have already been implemented and are used in actors' motion digitizing systems. Currently there are three types of such systems—mechanical, electromagnetic and optical (for example, the products of companies X-IST Realtime Technologies GmbH, Ascension Technology Corporation, Polhemus, Inc and others).

The implementation of the tactile feedback elements does not also involve a difficulty. The similar devices have already been developed. For example, an interface called GyroCube-Sensuous which is capable of rendering such feelings as "push, traction and jiggle" which is designed by a Japanese Institute (Japan's National Institute of Advanced Industrial Science and Technology—AIST) in conjunction with the University of Tsukuba.

An analysis of the coincidence of the motion trajectory of body parts and the reference movement in order to detect the areas of critical difference in the trajectories to send out a feedback signal is, in the author's view, a mainly trivial programming problem.

Setting the data exchange between the TRAINING SIMULATOR elements at the current state of art is the same trivial problem.

It is thus shown that there are no fundamental difficulties to implement the TRAINING SIMULATOR. The TRAINING SIMULATOR can be implemented by a plurality of concrete embodiments including with regard to what particularly field of learning activity it will be used in.

Although the preferred embodiment of the invention has been stated and illustrated, it is clear that the invention is not confined with it. Without moving away from the essence and the scope of the present invention determined in accordance with the following claims, the experts in this art recognize multiple modifications, changes, variations, replacements and equivalents.

The invention claimed is:

1. A method for providing a trainee with tactile feedback during training, comprising
    digitizing a movement by the trainee when the trainee is learning said movement;
    comparing the digitized movement of the trainee with a digitized reference movement;
    providing a deviation corridor for said digitized reference movement,
    said deviation corridor comprising a deviation operation threshold specified for said digitized reference movement;
    if a spatial movement of the trainee deviates from the deviation corridor such that the deviation operation threshold for the reference movement is exceeded, providing a tactile signal to one or more body parts of the trainee;
    wherein said tactile signal, through a combination of vibration elements that are simultaneously switched on with different levels of force and applied to a single body part, specifies the direction that the one or more body parts of the trainee must move to return to within deviation operation threshold of the deviation corridor.

2. The method according to claim 1, wherein the digitized pattern of the reference movement is obtained by digitizing an expert's movements.

3. The method according to claim 1, wherein the digitized reference movement is obtained by computer simulation.

4. The method according to claim 1, wherein the digitized reference movement is obtained by digitizing said trainee's movements.

5. The method according to claim 1, wherein the deviation operation threshold diminishes as the movement is mastered.

6. The method according to claim 1, wherein the intensity of the tactile signal increases as the deviation of the trainee's movement from the deviation corridor of the digitized reference movement enlarges.

7. The method according to claim 1, wherein the tactile signal is fed to the surface of a body lying opposite a right trajectory.

8. The method according to claim 1, wherein the tactile signal is fed to the surface of a body which is closest to a right trajectory.

9. The method according to claim 1, wherein as the frequency of exceeding the deviation operation threshold diminishes, the pace of the reference movement increases.

10. The method according to claim 1, wherein the movements to be learned by the trainee repeat periodically in blocks, and as the frequency of exceeding the deviation operation threshold diminishes, the number of movements repeated per block increases.

11. The method according to claim 1, wherein the pace of the reference movement is specified by a sound signal.

12. The method according to claim 1, wherein the pace of the reference movement is specified by an optical signal.

13. The method according to claim 1, wherein the reference movement is specified by a trainer.

14. The method according to claim 1, wherein the reference movement is specified by a video sequence.

15. The method according to claim 1, wherein the reference movement is specified on a computer screen.

16. The method according to claim 1, wherein the reference movement is specified in a printed form.

17. The method according to claim 1, wherein if a trainee's movement deviates from the reference movement, the trainee is given a pause to find a correct position at a particular stage of the reference movement, after which the reference movement goes on.

18. A device for implementing a training method, said device comprising:
    sensors for digitizing a movement of a trainee to obtain a digitized movement; and
    a computer for comparing the obtained digitized movement with a digitized pattern of a reference movement;
    wherein thermal elements are used for simultaneously applying different levels of heat to a single body part of the trainee for specifying the direction that the single body part must move to return to within a deviation corridor specified for the digitized pattern of the reference movement.

19. The device according to claim 18, wherein optical sensors are used for movement digitizing.

20. The device according to claim 18, wherein mechanical sensors are used for movement digitizing.

21. The device according to claim 18, wherein magnetic sensors are used for movement digitizing.

22. The device according to claim 18, wherein at least one of micromechanical accelerometers and micromechanical gyroscopes-based sensors are used for movement digitizing.

23. The device according to claim 18, wherein optical fiber-based sensors are used for movement digitizing.

24. The device according to claim 18, wherein Doppler effect-using sensors are used for movement digitizing.

25. The device according to claim 18, wherein sensors using a time of wave travel from a point with known coordinates to the sensor to set the coordinates of body parts are used for movement digitizing.

26. The device according to claim 18, wherein a combination of optical, mechanical, magnetic sensors, micromechanical accelerometers, micromechanical gyroscopes-based sensors, optical fiber-based sensors, sensors using Doppler effect for setting coordinates, or time of signal travel from a source with known coordinates to the sensor is used for movement digitizing.

27. The device according to claim 18, wherein mechanisms that apply pressure to the body parts of the trainee are used for applying different levels of pressure for specifying the direction that the body parts of the trainee must move to return to within a deviation corridor specified for the digitized pattern of the reference movement.

28. The device according to claim 18, wherein one or more tactile elements are used for each part of the trainee's body.

29. The device according to claim 18, wherein the device elements are connected by a wired data bus line.

30. The device according to claim 18, wherein the device elements are connected by a wireless data bus line.

31. The device according to claim 18, wherein said device is capable of digitizing the movement on one device and promptly transmitting the digitized movement to another similar device as a reference movement.

32. The device according to claim 18, wherein said device comprises a communication with a computer allowing synchronizing of the movements and their rate specified on a computer monitor and a reference movement pattern in the device.

33. The method according to claim 1, wherein said combination of vibration elements provide force on a side of the part of the trainee's body where the deviation threshold was exceeded so as to pull the part of the trainee's body to return within the deviation operation threshold of the deviation corridor.

34. The method according to claim 1, wherein said combination of vibration elements provide force on an opposite side of the part of the trainee's body where the deviation threshold was exceeded so as to push the part of the trainee's body to return within the deviation operation threshold of the deviation corridor.

35. The device according to claim 18, wherein said thermal elements provide force on a side of the part of the trainee's body where the deviation threshold was exceeded so as to pull the part of the trainee's body to return within the deviation operation threshold of the deviation corridor.

36. The device according to claim 18, wherein said thermal elements provide force on an opposite side of the part of the trainee's body where the deviation threshold was exceeded so as to push the part of the trainee's body to return within the deviation operation threshold of the deviation corridor.

37. The device according to claim 18, further comprising a combination of vibration elements that apply simultaneously different levels of force for specifying the direction that one or more body parts of the trainee must move in to return to within a deviation corridor specified for the digitized pattern of the reference movement, wherein the one or more body parts are different from the single body part that different levels of heat from the thermal elements are applied to.

38. A device for implementing a training method, said device comprising:
sensors for digitizing a movement of a trainee to obtain a digitized movement; and
a computer for comparing the obtained digitized movement with a digitized pattern of a reference movement;
wherein electric current discharges are used for simultaneously applying different levels of electric current to a single body part of the trainee for specifying the direction that the single body part must move to return to within a deviation corridor specified for the digitized pattern of the reference movement.

39. The device according to claim 38, wherein optical sensors are used for movement digitizing.

40. The device according to claim 38, wherein mechanical sensors are used for movement digitizing.

41. The device according to claim 38, wherein magnetic sensors are used for movement digitizing.

42. The device according to claim 38, wherein at least one of micromechanical accelerometers and micromechanical gyroscopes-based sensors are used for movement digitizing.

43. The device according to claim 38, wherein optical fiber-based sensors are used for movement digitizing.

44. The device according to claim 38, wherein Doppler effect-using sensors are used for movement digitizing.

45. The device according to claim 38, wherein sensors using a time of wave travel from a point with known coordinates to the sensor to set the coordinates of body parts are used for movement digitizing.

46. The device according to claim 38, wherein a combination of optical, mechanical, magnetic sensors, micromechanical accelerometers, micromechanical gyroscopes-based sensors, optical fiber-based sensors, sensors using Doppler effect for setting coordinates, or time of signal travel from a source with known coordinates to the sensor is used for movement digitizing.

47. The device according to claim 38, wherein mechanisms that apply pressure to the body parts of the trainee are used for applying different levels of pressure for specifying the direction that the body parts of the trainee must move to return to within a deviation corridor specified for the digitized pattern of the reference movement.

48. The device according to claim 38, wherein one or more tactile elements are used for each part of the trainee's body.

49. The device according to claim 38, wherein the device elements are connected by a wired data bus line.

50. The device according to claim 38, wherein the device elements are connected by a wireless data bus line.

51. The device according to claim 38, wherein said device is capable of digitizing the movement on one device and promptly transmitting the digitized movement to another similar device as a reference movement.

52. The device according to claim 38, wherein said device comprises a communication with a computer allowing synchronizing of the movements and their rate specified on a computer monitor and a reference movement pattern in the device.

53. The device according to claim 38, wherein said electric current discharges provide force on a side of the part of the trainee's body where the deviation threshold was exceeded so as to pull the part of the trainee's body to return within the deviation operation threshold of the deviation corridor.

54. The device according to claim 38, wherein said electric current discharges provide force on an opposite side of the part of the trainee's body where the deviation threshold was exceeded so as to push the part of the trainee's body to return within the deviation operation threshold of the deviation corridor.

55. The device according to claim 38, further comprising a combination of vibration elements that apply simultaneously different levels of force for specifying the direction that one or more body parts of the trainee must move in to return to within a deviation corridor specified for the digitized pattern of the reference movement, wherein the one or more body parts are different from the single body part that different levels of electric current from the electric current discharges are applied to.

* * * * *